United States Patent
Dawson et al.

(10) Patent No.: US 6,340,587 B1
(45) Date of Patent: Jan. 22, 2002

(54) PROCESS FOR PREPARING ENANTIOMERICALLY ENRICHED N-DERIVATIZED LACTAMS

(75) Inventors: Michael John Dawson, Mitchin; Mahmoud Mahmoudian, London; Christopher John Wallis, Royston, all of (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/446,587

(22) PCT Filed: Aug. 20, 1998

(86) PCT No.: PCT/EP98/05291

§ 371 Date: Feb. 14, 2000

§ 102(e) Date: Feb. 14, 2000

(87) PCT Pub. No.: WO99/10519

PCT Pub. Date: Mar. 4, 1999

(30) Foreign Application Priority Data

Aug. 22, 1997 (GB) .............................................. 9717928

(51) Int. Cl.⁷ ................................................ C07C 1/04
(52) U.S. Cl. ....................................................... 435/280
(58) Field of Search .......................................... 435/280

(56) References Cited

U.S. PATENT DOCUMENTS 6,156,893 A * 12/2000 Bernegger et al. .......... 544/277

FOREIGN PATENT DOCUMENTS

EP 0424064 A1 4/1991
WO WO92/ 18477 10/1992

OTHER PUBLICATIONS

Enzyme Nomenclature, Academic Press, Inc., pp. 330, 344–347, 366–369 (1984).*
Evans et al, J Chem Soc Perkin Trans I, 1992, 0 (5), pp.589–592, "Potential use of carbocyclic nucleosides for the treatment of aids . . . ".
Nakano et al, Tetrahedron; Asymmetry, 1994, 5 (7), pp.1155–1156, "A facile lipase–catalyzed resolution . . . ".
Nakano, et al, Tetrahedron; Asymmetry, 1996, 7 (8), pp.2381–2386, "Lipase–catalyzed resolution . . . ".

* cited by examiner

Primary Examiner—Sandra E. Saucier
(74) Attorney, Agent, or Firm—Amy H. Fix

(57) ABSTRACT

The present invention relates to a process for the preparation of enantiomerically enriched N-derivatized (1R,4S)-2-azabicyclo[2.2.1]hept-5-en-3-ones by use of an enzyme.

14 Claims, No Drawings

PROCESS FOR PREPARING ENANTIOMERICALLY ENRICHED N-DERIVATIZED LACTAMS

FIELD OF THE INVENTION

The present invention relates to a process for the preparation of enantiomerically enriched N-derivatised (1R,4S)-2-azabicyclo[2.2.1]hept-5-en-3-ones.

BACKGROUND OF THE INVENTION

Abacavir, a 2-aminopurine nucleoside analogue with the following structure (I)

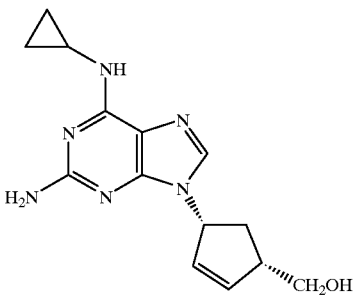

(I)

known from EP 0434 450, has potent activity against human immunodeficiency virus (HIV) and hepatitis B virus (HBV).

There exists a need to synthesise large quantities of abacavir for clinical trials. In the future, once abacavir has been approved by the national medicine regulatory agencies, large quantities of abacavir will also be required for sale as a prescription medicine for the treatment of HIV infections.

An important step in the manufacture of abacavir is the preparation of an enantiomerically pure substituted cyclopentene ring. Existing methods are known which commence from a lactam of formula (II)

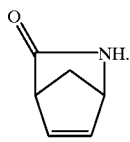

(II)

EP-A-0424064 describes a process wherein the racemic lactam (II) prepared by the reaction of cyclopentadiene with tosyl cyanide, can be reacted with lactamases that will give a single cis enantiomer, or a mixture of cis enantiomers which is enriched with respect to one of the enantiomers, of the ring-opened compound (III)

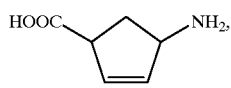

(III)

together with unreacted lactam which is enantiomerically enriched with respect to one or other enantiomer.

SUMMARY OF THE INVENTION

We have now developed a high yielding and cost effective process for the production of substantially enantiomerically pure intermediates of formula (IV)

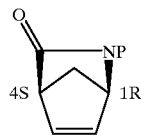

(IV)

wherein P is an activating and protecting group from their racemates.

We have found that derivatisation of the lactam nitrogen atom in the compound of formula (II) with a group P [as in formula (V) below] activates the lactam bond for hydrolysis. We have surprisingly found that enzymes more readily obtainable than those described in EP-A-0424064 and which appear, under normal conditions, to have no activity in relation to the lactam of formula (II) described in EP-A-0424064 can be used to produce compounds of formula (IV).

According to one aspect of the present invention, therefore, we provide a process for the enantiomeric resolution of a racemic mixture of N-protected (±) 2-azabicyclo[2.2.1]hept-5-en-3-one (V)

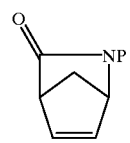

(V)

wherein P is an activating and protecting group, to yield substantially enantiomerically pure N-protected (1R,4S)-2-azabicyclo[2.2.1]hept-5-en-3-one (IV) by treating the mixture with an acylase enzyme.

According to a further aspect of the present invention, we provide a process for the preparation of substantially enantiomerically pure N-protected (1R,4S)-2-azabicyclo[2.2.1]hept-5-en-3-one of formula (IV), above, wherein P is an activating and protecting group, wherein a racemic mixture of N-protected (±) 2-azabicyclo[2.2.1]hept-5-en-3-one of formula (V), above, wherein P is an activating or protecting group, is treated with an acylase enzyme and the unreacted enantiomer of formula (IV) is isolated from the reaction mixture by conventional techniques.

DETAILED DESCRIPTION OF THE PREFERRED EMBODIMENT

It is preferred that the activating/protecting group is an acyl or substituted oxycarbonyl group. Preferred acyl groups include formyl or lower alkanoyl (having e.g. 1 to 4 carbon atoms in the alkyl portion), especially an acetyl group. Preferred substituted oxycarbonyl groups will be of the formula ROC(O)—, wherein R may be an alkyl or aralkyl group. A preferred alkyl group is tert butyl. A possible aralkyl group is benzyl.

Since we have also found that substantial deprotection of these acyl-protected compounds can occur under aqueous conditions, it is preferred that the reaction is carried out in a mixture of organic solvent and water. It is preferred to use water miscible organic solvents, such as cyclic ethers e.g. tetrahydrofuran or 1,4-dioxan. To minimise deprotection it is preferred to use less than 70% water, more preferably around 50% or less (by volume). A mixture of tetrahydrofuran and water of approximately 50:50 (v/v) has been found most suitable.

When used as above the reaction may generally take place in a single phase. However, there is no reason why use of an organic solvent to create a bi-phasic system would not also be successful, such as with aromatic hydrocarbons.

Upon completion of the reaction the unreacted and essentially enantiomerically pure N-protected (1R,4S)-2-azabicyclo[2.2.1]hept-5-en-3-one of formula (IV) can be isolated from the reaction mixture by conventional techniques, such as solvent extraction.

A number of acylase enzymes have been found which enantioselectively hydrolyse the lactam bond so as to leave behind the desired isomer. We have found enzymes derived from Bacillus sp. in particular to show the right profile of activity. For example, *Subtilisin carlsberg* (ALTUS) yields N-protected (1R,4S)-2-azabicyclo[2.2.1]hept-5-en-3-one [(IV), P=tert butyl oxycarbonyl] from the racemic mixture (V) in an enantiomeric excess of 73%. Other enzymes include Bacillus sp. protease, Neutrase, Novozyme 243, Alcalase and Savinase, and are available commercially from ALTUS and NOVO. Enzymes from other sources which show enantioselective hydrolysis may also be used, such as pig liver esterase (ALTUS), porcine pancreatic lipase (Biocatalysts), Flavorpro-192 (peptidase, Biocatalysts), Flavorpro-373 (glutaminase, Biocatalysts), Promod-TP (endopeptidase, Biocatalysts), lipase-CE (*Humicola lanuginosa*, Amano), protease-M (Aspergillus sp., Amano), prozyme-6 (Aspergillus sp., Amano), lipase PGE (calf root and salivary gland, Amano) and Aspergillus sp. acylase (Sigma).

Preferably, the commercially available acylase enzyme Savinase (NOVO) will be used as this has in particular been found to show bioconversion rates of the N-protected (1S, 4R)-2-azabicyclo[2.2.1]hept-5-en-3-one suitable for industrial scale applications. Savinase is a proteolytic enzyme prepared by submerged fermentation of an alkalophilic species of Bacillus. It is an endoprotease of the serine type. In tests that we have carried out, this enzyme has not shown any ability to hydrolyse a racemic mixture of the unacylated lactam of formula (II), under normal use conditions.

Bioconversion of the N-protected (1S,4R)-2-azabicyclo[2.2.1]hept-5-en-3-one will desirably be carried out within a pH range of 6 to 11, preferably 7 to 9. A temperature within the range of 20 to 50° C. will preferably be used. It is most preferred to carry out the process at a pH of about 8 and a temperature of about 30° C. A ratio of Savinase:substrate in the range of from 1:1 to 10:1 e.g. from 2:1 to 5:1 (w/w) produces a clean, rapid reaction. The optimum ratio for a given enzyme can readily be determined by simple experimentation.

The starting compounds of formula (V) in which P is tert butyloxycarbonyl may be prepared from the corresponding unprotected racemic lactam of formula (II) by methods analogous to those described in Taylor et al., Tet. Asymmetry, 4, p.1117 (1993). Compounds of formula (V) in which P is formyl or lower alkanoyl may be prepared from the corresponding unprotected racemic lactam of formula (II) by methods as described in T. W. Greene, "Protective Groups in Organic Synthesis", Wiley, New York, 1981, pp. 218–287 and J. F. W. McOmie, "Protective Groups in Organic Chemistry", Plenam Press, New York, 1973, pp. 43–93, or by analogous methods.

The compound of formula (IV) may readily be converted to the corresponding N-protected amino acid by hydrolysis. The N-protected amino acid can readily be converted to the corresponding amino alcohol of formula (VI)

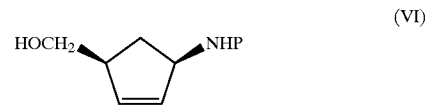

by reagents capable of converting carboxylic acids to alcohols, for example lithium aluminium hydride or borane. Alternatively, the compound of formula (IV) may be directly converted into the corresponding ring-opened amino alcohol of formula (VI) by using sodium borohydride by methods such as described in Tet. Asymm, 4, p. 1117 (1993).

The following Examples are intended for illustration only and are not intended to limit the scope of the invention in any way.

EXAMPLE 1

Several hydrolytic enzymes were screened for the ability to hydrolyse the lactam bond of racemic (±) tert butyl 3-oxo-2-azabicyclo[2.2.1]hept-5-ene-2-carboxylate [(V), P=tert butyl oxycarbonyl] enantioselectively. Reactions were carried out at room temperature in magnetically-stirred glass vials (4 ml working volume) containing 1 mg/ml of the racemic compound in 50% tetrahydrofuran: 50% phosphate buffer (v/v) (50 mM, pH 7) at room temperature. Each enzyme was added to give a final concentration of 25 mg/ml. This represents a 25:1 ratio (w:w) of enzyme to substrate which for screening purposes should detect any possible hydrolytic activity. Flasks with no enzyme served as controls. Periodically, samples were removed and diluted 1:2 with water prior to hplc analysis.

hplc condition: Column: Spherisorb C6 (15×0.46 cm). Isocratic at room temperature at 1 ml/min. Mobile phase: 30% (v/v) acetonitrile containing 0.1% (v/v) formic acid. Detection wavelength at 200 nm.

It was shown that chemical hydrolysis of (±) tert butyl 3-oxo-2-azabicyclo[2.2.1]hept-5-ene-2-carboxylate was negligible under the reaction conditions. Several enzymes appeared to hydrolyse the racemic compound enantioselectively to afford (−) (1R, 4S) tert butyl 3-oxo-2-azabicyclo[2.2.1]hept-5-ene-2-carboxylate as evidenced by a negative sign of rotation by chiralyser (HPLC optical rotation detector). Savinase was chosen for further investigation. The reaction mixture, containing approximately 50% of the starting material, was analysed by chiral hplc and the residual lactam was shown to have an enantiomeric excess of 96.3%.

Furthermore the residual substrate was of the correct absolute configuration for the synthesis of abacavir.

Chiral hplc: Column: Chiralcel OD-H(25×0.46 cm). Isocratic at 50° C. at 0.5 ml/min. Mobile phase: 2% (v/v) isopropyl alcohol/heptane. Detection wavelength at 205 nm.

COMPARATIVE EXAMPLE 1

A solution containing racemic lactam (±) 2-azabicyclo [2.2.1]hept-5-en-3-one (II) at 1 mg/ml (4 ml working volume) was treated with Savinase (obtainable from NOVO) (25 mg/ml) in 50% tetrahydrofuran: 50% phosphate buffer (50 mM, pH 7). A flask with no enzyme served as control. Periodically, samples were removed and diluted 1:2 with water prior to hplc analysis.

hplc: Column: Spherisorb C6 (15×0.46 cm). Isocratic at room temperature at 1 ml/min. Mobile phase: 4% (v/v)

acetonitrile containing 0.1% (v/v) formic acid. Detection wavelength at 200 nm.

There was no reaction after 4 days incubation at room temperature.

EXAMPLE 2

Savinase (30 g, NOVO) was added to a solution (500 ml) containing 10 g of racemic (±) tert butyl 3-oxo-2-azabicyclo [2.2.1]hept-5-ene-2-carboxylate [(V), P=tert butyl oxycarbonyl] in 50:50 (v/v) tetrahydrofuran/50 mM phosphate pH 8.0 at 30° C. The reaction was monitored by chiral HPLC for up to 2 days.

Upon completion of the reaction (ca. 51% conversion, enantiomeric excess of (−) (1R, 4S) tert butyl 3-oxo-2-azabicyclo[2.2.1]hept-5-ene-2-carboxylate >99.8%), the enzyme was filtered and the pH of the clarified solution was raised to 9 with sodium bicarbonate solution. This was then extracted with 3×200 ml of cyclohexane. The combined organic phase was back extracted with 100 ml of sodium bicarbonate solution and subsequently washed with 100 ml of brine. Evaporation and drying yielded a free flowing white solid (4.2 g, 84% theory isolated yield). This was identified as (−) (1R, 4S) tert butyl 3-oxo-2-azabicyclo [2.2.1]hept-5-ene-2-carboxylate by NMR; enantiomeric excess >99.8% by chiral HPLC.

Chiral hplc: Column: Chiralcel OD-H(25×0.46 cm). Isocratic, 0.5 ml/min. Mobile phase: 2% (v/v) isopropyl alcohol/heptane. Detection wavelength at 205 nm. Temperature at 5° C.

EXAMPLE 3

A solution of the above (−) (1R, 4S) tert butyl 3-oxo-2-azabicyclo[2.2.1]hept-5-ene-2-carboxylate (3.5 g) in tetrahydrofuran (10 ml) was added to a suspension of sodium borohydride (1.27 g) in methanol (10 ml) and the mixture was stirred at about 20° C. for about 18 hours. A further quantity of tetrahydrofuran (10 ml) and sodium borohydride (1.27 g) were added and stirring was continued for about a further 2 hours. 2 Molar hydrochloric acid (30 ml) was cautiously added, followed by toluene (20 ml). The two layers were separated, and the aqueous layer was further extracted with toluene (2×25 ml). The combined organic extracts were washed with brine (20 ml), dried over sodium sulfate and evaporated to afford (1R, 4S) (4-hydroxymethyl)-cyclopent-2-en-1-yl carbamic acid tert butyl ester (3.23 g) with an enantiomeric excess of 99.2% by chiral hplc as a pale yellow gum, which was spectroscopically and chromatographically identical to an authentic sample.

Chiral hplc: Column: Chiralcel OD (25×0.46 cm). Flow: 1.0 ml/min. Mobile phase: 3% (v/v) isopropyl alcohol/heptane. Detection wavelength at 205 nm. Temperature at 35° C.

EXAMPLE 4

Savinase was tested for the ability to hydrolyse the lactam bond of racemic cis-2-acetyl-2-aza-bicyclo[2.2.1]hept-5-en-3-one enantioselectively. Reaction was carried out in a magnetically-stirred glass vial (4 ml working volume) containing 1 mg/ml of substrate in 50% tetrahydrofuran: 50% phosphate buffer (v/v) (50 mM, pH 7) at room temperature. Reaction was started by adding Savinase to a final concentration of 25 mg/ml. A flask with no enzyme served as control. Periodically, samples were removed and diluted 1:2 with water prior to hplc analyses.

hplc: Column: Spherisorb C6 (15×0.46 cm). Isocratic at 20° C. at 1 ml/min. Mobile phase: 5% (v/v) acetonitrile containing 0.1% (v/v) formic acid. Detection wavelength at 210 nm.

Chiral hplc: Column: Chiralpak AD (25×0.46 cm). Isocratic at 20° C. at 1 ml/min. Mobile phase: 2% (v/v) ethanol/heptane. Detection wavelength at 215 nm.

It was shown that, in the absence of enzyme, chemical hydrolysis of the substrate was negligible under reaction conditions. However, there was a significant non-enzymic hydrolysis of the substrate if tetrahydrofuran was omitted from reaction mixtures. Savinase hydrolysed racemic cis-2-acetyl-2-aza-bicyclo[2.2.1]hept-5-en-3-one enantioselectively to afford (−) (1R, 4S) 2-acetyl-2-aza-bicyclo[2.2.1] hept-5-en-3-one as evident by a negative sign of rotation by chiralyser and by chiral hplc analysis. The reaction mixture, containing approximately 50% of the starting material was analysed by chiral hplc after two days and the residual lactam was shown, by comparison with an authentic sample, to have an enantiomeric excess of >99.8% with the correct absolute configuration for the synthesis of abacavir.

What is claimed is:

1. A process for the preparation of substantially enantiomerically pure N-protected (1R,4S)-2-azabicyclo[2.2.1] hept-5-en-3-one of formula (IV)

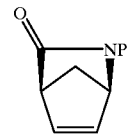

(IV)

wherein P is an activating and protecting group, wherein a racemic mixture of N-protected (±) 2-azabicyclo [2.2.1]hept-5-en-3-one (V)

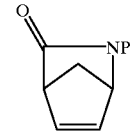

(V)

wherein P is an activating or protecting group, is treated with an acylase enzyme and the unreacted enantiomer of formula (IV) is isolated from the reaction mixture by conventional techniques.

2. A process for the enantiomeric resolution of a racemic mixture of N-protected (±) 2-azabicyclo[2.2.1]hept-5-en-3-one (V)

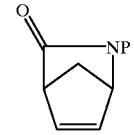

(V)

wherein P is an activating and protecting group,
to yield substantially enantiomerically pure N-protected (1R,4S)-2-azabicyclo[2.2.1]hept-5-en-3-one (IV)

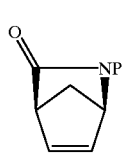
(IV)

wherein P is an activating and protecting group,
by treating the mixture with an acylase enzyme.

3. A process as claimed in claim 1 or wherein P is an acyl or oxycarbonyl group.

4. A process as claimed in any of claims 1 to 3 wherein P is a formyl or alkanoyl group having 1 to 4 carbon atoms.

5. A process as claimed in claim 1 wherein P is an alkyloxycarbonyl or aralkyloxycarbonyl group.

6. A process as claimed in claim 5 wherein P is a tert butyloxycarbonyl or benzyloxycarbonyl group.

7. A process as claimed in claim 1 wherein the acylase enzyme is derived from Bacillus sp.

8. A process as claimed in claim 7 wherein the acylase enzyme is Savinase.

9. A process as claimed in claim 1 wherein the reaction is carried out in a mixture of organic solvent and water.

10. A process as claimed in claim 9 wherein the organic solvent is a water miscible organic solvent and less than 70% water by volume is used.

11. A process as claimed in claim 10 wherein the water miscible organic solvent is tetrahydrofuran or 1,4-dioxan.

12. A process as claimed in claim 1 wherein the reaction is carried out within a pH range of 6 to 11 and at a temperature of 20 to 50° C.

13. A process as claimed in claim 12 wherein the reaction is carried out at a pH of about 8 and a temperature of about 30° C.

14. A process as claimed in claim 1 wherein the unreacted N-protected (1R,4S)-2-azabicyclo[2.2.1]hept-5-en-3-one of formula (IV) is isolated by solvent extraction.

* * * * *